United States Patent
Cao

(10) Patent No.: US 11,540,881 B2
(45) Date of Patent: Jan. 3, 2023

(54) MICROWAVE ABLATION PROBE WITH RADIOFREQUENCY IMPEDANCE SENSING

(71) Applicant: Boston Scientific Scimed, Inc., Maple Grove, MN (US)

(72) Inventor: Hong Cao, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 646 days.

(21) Appl. No.: 16/541,922

(22) Filed: Aug. 15, 2019

(65) Prior Publication Data

US 2020/0060761 A1 Feb. 27, 2020

Related U.S. Application Data

(60) Provisional application No. 62/721,698, filed on Aug. 23, 2018.

(51) Int. Cl.
*A61B 18/18* (2006.01)
*A61B 34/10* (2016.01)
*A61B 18/00* (2006.01)

(52) U.S. Cl.
CPC .......... *A61B 18/1815* (2013.01); *A61B 34/10* (2016.02); *A61B 2018/00023* (2013.01); *A61B 2018/0066* (2013.01); *A61B 2018/00577* (2013.01); *A61B 2018/00702* (2013.01)

(58) Field of Classification Search
CPC .................................................. A61B 18/1815
See application file for complete search history.

(56) References Cited

U.S. PATENT DOCUMENTS

| 6,962,587 B2 | 11/2005 | Johnson et al. |
| 8,246,615 B2 | 8/2012 | Behnke |
| 8,279,604 B2 | 10/2012 | Jones et al. |
| 9,820,814 B2 | 11/2017 | Turovskiy et al. |
| 2001/0003798 A1 | 6/2001 | Mcgovern et al. |

(Continued)

FOREIGN PATENT DOCUMENTS

| JP | 200137776 A | * | 2/2001 | ......... A61B 18/1815 |
| JP | 2001037775 | | 2/2001 | |

(Continued)

OTHER PUBLICATIONS

"International Preliminary Report on Patentability," for PCT Application No. PCT/US2019/047062 dated Mar. 4, 2021 (9 pages).

(Continued)

*Primary Examiner* — Ronald Hupczey, Jr.
(74) *Attorney, Agent, or Firm* — Pauly, DeVries Smith & Deffner LLC

(57) ABSTRACT

A microwave ablation system and method include an elongate microwave ablation probe. The probe has a radiating portion for performing microwave ablation. The probe includes a first electrode and a second electrode located along the probe body. A radiofrequency energy source is connected to the first and second electrodes. An impedance of tissue is measured using the first and second electrodes. The impedance is used to detect a change in tissue due to microwave ablation of the tissue. Therapy parameters for the microwave ablation procedure can be adjusted in response to the measured impedance. In some examples, one of the electrodes is proximal and one electrode is distal to the radiating portion.

20 Claims, 9 Drawing Sheets

(56) References Cited

U.S. PATENT DOCUMENTS

| | | | |
|---|---|---|---|
| 2006/0074413 A1* | 4/2006 | Behzadian | A61B 18/1477 606/41 |
| 2010/0125269 A1 | 5/2010 | Emmons et al. | |
| 2010/0217253 A1 | 8/2010 | Mehta | |
| 2011/0208184 A1 | 8/2011 | Brannan | |
| 2012/0203217 A1 | 8/2012 | Brannan | |
| 2014/0296841 A1* | 10/2014 | Brannan | A61B 18/1815 606/33 |
| 2015/0133910 A1 | 5/2015 | Brannan | |

FOREIGN PATENT DOCUMENTS

| | | |
|---|---|---|
| JP | 2001037776 | 2/2001 |
| JP | 2012161603 | 8/2012 |
| WO | 2017174513 | 10/2017 |
| WO | 2020041195 | 2/2020 |

OTHER PUBLICATIONS

"Response to Communication Pursuant to Rules 161(1) and 162 EPC," for European Patent Application No. 19759875.8 filed Sep. 14, 2021 (10 pages).

"International Search Report and Written Opinion," for PCT Application No. PCT/US2019/047062 dated Oct. 29, 2019 (14 pages).

"Advancing Ablation Boundaries," RFA Medical Technology and Product Information accessed from website URL <www.rfamedical.com> on Sep. 10, 2019 (2018) 4 pages.

Brace, Christopher "Microwave Tissue Ablation: Biophysics, Technoogy, and Applications," Critical Reviews in Biomedical Engineering, 38(1): 65-78 (2010) (14 pages).

"Delivering Energy Innovation: The New Cool-tip RF Ablation System E Series," Coviden Cool-tip Product Brochure Feb. 2014 (4 pages).

"Leveen Needle Electrodes," Boston Scientific Corporation product information for Leveen Needle Electrode Family, Jul. 2015 (2 pages).

Narayanan, G. et al., "Radiofrequency Ablation: Current Status," Boston Scientific Corporation Technique Spotlight, Jun. 2015 (8 pages).

"OsteoCool RF Ablation System and Bone Access Kits," Medtronic Surgical Technique Guide 2019 (16 pages).

"OsteoCool RF Ablation System," Medtronic Product Brochure 2019 (6 pages).

"Rf 3000 Generator," Boston Scientific Corporation Product Brochure, Jun. 2015 (6 pages).

"StarBurst XL Radiorequency Ablation Alectrodes," Angiodynamics Product Brochure, 2013 (2 pages).

"Office Action," for Japanese Patent Application No. 2021-509858 dated Mar. 1, 2022 (14 pages), with English translation.

* cited by examiner

MICROWAVE ABLATION PROBE WITH RADIOFREQUENCY IMPEDANCE SENSING

This application claims the benefit of U.S. Provisional Application No. 62/721,698, filed Aug. 23, 2018, the content of which is herein incorporated by reference in its entirety

BACKGROUND

Microwave ablation (MWA) is a minimally invasive energy modality for body treatments in many locations, including soft tissue lesions in the liver, kidney and lung. Microwave ablation probes use an antenna, such as a monopole or dipole antenna, to radiate microwave energy into tissue for heating. Unlike radiofrequency ablation, which depends on ion movement and friction for heating, microwave ablation energy causes water molecules to rotate due to the polarity of the molecules and generates heat due to hysteresis. It typically operates at industrial, scientific and medical (ISM) radio bands such as 500 MHz to 10 GHz, and more specifically can operate at 945 MHz or 2.45 GHz. Microwave ablation has advantages such as fast heating, allowing the probe to operate at high temperature to create larger lesions, and has been gaining market share over the past decade over radiofrequency ablation (RFA) for tissue ablation.

SUMMARY

Some examples of the disclosed technology provide a microwave ablation system having an elongate microwave ablation probe. In some examples the ablation probe includes a probe body with a radiation window that is at least partially transparent to microwave energy. The ablation probe also includes an antenna within the probe body, the antenna having a radiating portion for emission of microwave energy at a distal portion of the probe body, and the radiating portion is aligned with the radiation window. The ablation probe further includes a cable within the probe body connected to the antenna, and the cable has at least one conductor. The ablation probe further includes a first distal electrode located along the probe body distal to the radiation window, a first proximal electrode located along the probe body proximal to the radiation window, and a microwave energy source connected to the antenna via the cable. The disclosed technology further includes a radiofrequency energy source connected to the first distal electrode with a first distal lead and connected to the first proximal electrode with a first proximal lead. The system further includes a sensing circuit connected to the first distal electrode and first proximal electrode. The sensing circuit is configured to generate at least one signal corresponding to an impedance of tissue.

In some examples of the technology, the sensing circuit is configured to sense a first impedance between the first distal electrode and a reference patch on an external surface of a body and a second impedance between the first proximal electrode and the reference patch. In some examples of the technology, the sensing circuit is configured to sense a first bipolar impedance between the first distal electrode and the first proximal electrode. In some examples of the technology, the system further includes a second distal electrode located along the probe body distal to the radiation window. In some examples of the technology, the sensing circuit is configured to sense a first bipolar impedance between the first distal electrode and the second distal electrode. In some examples of the technology, the system includes a second proximal electrode located along the probe body proximal to the radiation window. In some examples of the technology, the sensing circuit is configured to sense a first bipolar impedance between the first proximal electrode and the second proximal electrode. In some examples of the technology, the sensing circuit is configured to sense a second bipolar impedance between the first distal electrode and the first proximal electrode, and a third bipolar impedance between the first distal electrode and the second proximal electrode. In some examples of the technology, the first proximal electrode is a choke of the microwave ablation probe disposed around the probe body. In some examples of the technology, the first distal electrode or first proximal electrode comprises a band located on an exterior surface of the probe body. In some examples of the technology, the probe body further comprises a microwave shielding structure defining the radiation window, and the first distal lead and first proximal lead are electrically isolated from the antenna, and the first distal lead and the first proximal lead are configured to be either underneath the microwave shielding structure, outside of the microwave shielding structure and underneath an insulation layer, or a conductive trace on an outside surface of the microwave shielding structure.

Some further examples of the disclosed technology provide a microwave ablation system having an elongate microwave ablation probe that includes a probe body comprising a radiation window that is at least partially transparent to microwave energy, an antenna within the probe body, the antenna having a radiating portion for emission of microwave energy at a distal portion of the probe body, wherein the radiating portion is aligned with the radiation window, a cable within the probe body, connected to the antenna, comprising at least one conductor, a first electrode located along the probe body, and a second electrode located along the probe body. The disclosed example further includes a microwave energy source connected to the antenna via the cable, a radiofrequency energy source connected to the first electrode with a first lead and connected to the second electrode with a second lead, and a sensing circuit connected to the first electrode and second electrode, the sensing circuit configured to generate at least one signal corresponding to an impedance of tissue, the system configured to use the impedance of tissue to detect a change in tissue due to microwave ablation.

In some examples of the technology, the first electrode is a first proximal electrode located along the probe body proximal to the radiation window and the second electrode is a second proximal electrode located along the probe body proximal to the radiation window. In some examples of the technology, the first electrode is a first distal electrode located along the probe body distal to the radiation window and the second electrode is a first proximal electrode located along the probe body proximal to the radiation window.

Some further examples of the disclosed technology provide a method of microwave ablation. The method includes the step of providing a microwave ablation system, which includes providing a probe having a probe body, an antenna having a radiating portion for emission of microwave energy, wherein the radiating portion is aligned with a window portion that is at least partially transparent to microwave energy, a first distal electrode located along the probe body distal to the window portion, and a first proximal electrode located along the probe body proximal to the window portion. The method further includes delivering microwave energy to the radiating portion, delivering radiofrequency energy to the first distal electrode and the first proximal electrode, and measuring an impedance of tissue using a sensing circuit connected to the first distal electrode and to the first proximal electrode. The method includes determining a tissue change using the impedance of tissue measured by the sensing circuit.

Some examples of the technology further include the step of sampling a first impedance at a first time, sampling a second impedance at a second time, and comparing the first impedance to the second impedance. Some examples of the technology further include the step of determining a microwave ablation treatment endpoint based on the comparison of the first impedance to the second impedance. Some examples of the technology further include the step of adjusting a therapy parameter based on the comparison of the first impedance to the second impedance, wherein the therapy parameter is the power provided to a microwave energy source or a time length of ablation procedure. Some examples of the technology further include the step of measuring a first impedance between the first distal electrode and a reference patch on an external surface of a body and measuring a second impedance between the first proximal electrode and the reference patch. Some examples of the technology further include the step of measuring an impedance between the first distal electrode and the first proximal electrode.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

While embodiments are susceptible to various modifications and alternative forms, specifics thereof have been shown by way of example and drawings and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Typically, a physician uses power and time to control ablation. However, this does not reflect the actual tissue ablation process. With radiofrequency ablation, as tissue loses moisture and undergoes necrosis, the impedance of the tissue increases. Radiofrequency energy cannot penetrate tissue with high impedance, which creates a physical limit to the size of lesions that can be created with radiofrequency ablation. With microwave ablation, there is no such physical limit because the microwave energy can propagate even when tissue is lacking in moisture or has undergone necrosis. A microwave ablation probe with systems for tissue assessment can more fully utilize the capability of microwave ablation.

The technology described herein provides one or more impedance sensing electrodes on the shaft of the microwave ablation probe. The electrodes allow radiofrequency impedance to be measured between the electrodes or between the electrodes and a grounding pad on a patient's body. This impedance measurement is used to monitor the tissue change during microwave ablation, and to control the microwave energy delivery during microwave ablation. A change in impedance represents a change in tissue around an individual electrode in the case of monopolar sensing, or between two electrodes in the case of bipolar radiofrequency sensing. As used herein, bipolar impedance refers to an impedance measured using bipolar radiofrequency sensing, and monopolar impedance refers to an impedance measured using monopolar radiofrequency sensing.

The measured impedances and changes in impedances over time allow the system to adjust the microwave energy delivery based on actual tissue changes within the tissue being ablated. In some examples, the system can be configured to monitor impedance during the microwave ablation procedure and discontinue ablation when a measured impedance reaches a threshold measurement. Alternatively, the endpoint of the treatment can be determined when a calculated change in impedance reaches a threshold.

Figure 1:
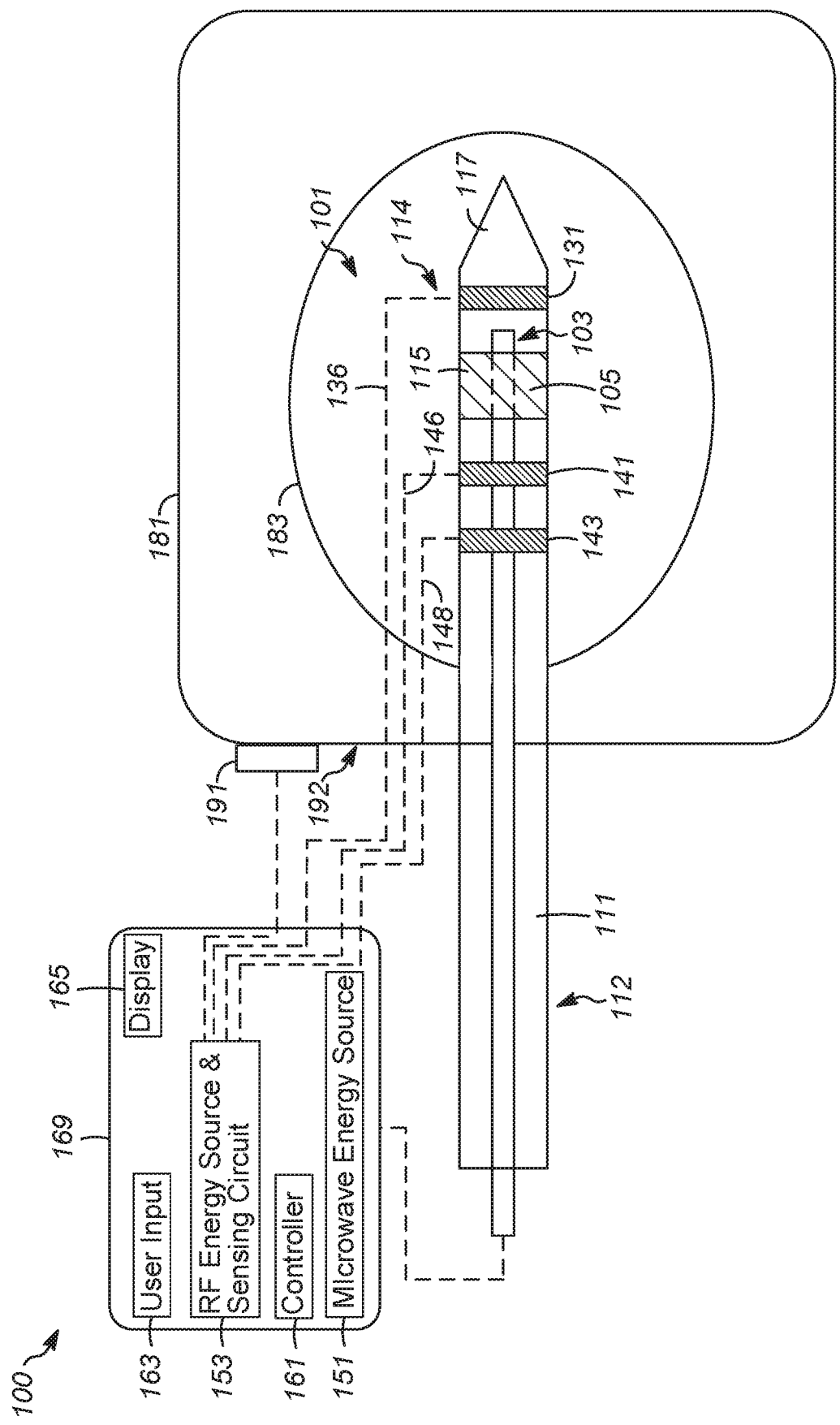
FIG. 1 is a schematic view of a microwave ablation system according to some examples.

In some examples of the disclosed technology, a microwave ablation system includes a probe having a microwave antenna with a radiating portion for emission of microwave energy. Turning to FIG. 1, a microwave ablation system 100 includes an elongate microwave ablation probe 101 having a probe body 111 with a proximal portion 112 and a distal portion 114. The probe 101 can be provided in a variety of lengths and are elongate in shape. The length of the probe body 111 is much larger than its diameter. For example, the length may be 10 times the diameter or more, 50 times the diameter or more, 100 times the diameter or more, or 200 times the diameter or more. The length may be at least 5 centimeters or at least 10 centimeters, in some examples. In some examples, the probe body 111 is constructed with stainless steel. Alternatively, the probe body can be constructed with braided PEBAX® elastomer, produced by Arkema Group, headquartered in Colombes, France. PEBAX® elastomers are block copolymers made up of rigid polyamide blocks and soft polyether blocks.

In some examples, the outer diameter of the probe body 111 is at least about 18 gauge (1.02 millimeters), at least about 17 gauge (1.15 millimeters), or at least about 16 gauge (1.29 millimeters). In some examples, the outer diameter of the probe body 111 is at most about 12 gauge (2.01 millimeters), at most about 13 gauge (1.83 millimeters), or at most about 14 gauge (1.63 millimeters).

The microwave ablation probe 101 can further include a handle and cables (not shown) to connect to a control system 169. The probe 101 further includes a window 115 that is at least partially transparent to microwave energy. The window 115 can be constructed, for example, using fluoropolymers, urethanes, polyether block amides (PEBA), polypropylene, polyethylene, polyamide (nylon), polyimide, polyetherimide (PEI), polysulfone, and polyetheretherketone (PEEK). In the example of FIG. 1, the window 115 is situated on the probe body 111 between a proximal end 112 and a distal end 114 of the probe 101. The length of the window portion 115 of the probe body 111 is based on the particular antenna used in the microwave ablation probe 101. In some examples, the length is at least about 7 millimeters, at least about 10 millimeters, or at least about 13 millimeters. In some examples, the length is at most about 30 millimeters, or at most about 20 millimeters. In one example, the length is about 15 millimeters.

In some examples of the technology, the probe 101 has a distal tip 117, which can be a trocar tip.

As used herein, the words proximal and distal are relative terms that describe a spatial relationship between two objects. An object described as being distal is positioned in a spatial relationship such that the distal object is closer to the distal end 114. An object described as being proximal is positioned in a spatial relationship such that the proximal object is closer to the proximal end 112.

The probe 101 includes a microwave antenna 103 within the probe body 111. In some examples, the microwave antenna 103 is a monopolar microwave ablation antenna. The microwave antenna 103 has a radiating portion 105. The radiating portion 105 is aligned with the window portion 115 of the probe body 111 such that microwave energy emitted from the radiating portion 105 can pass through the window portion 115 into the tissue to be ablated 183. The radiating portion 105 is generally located near a distal portion 114 of the probe body 111.

The probe 101 further includes a first distal electrode 131 located along the probe body 111 in a spatial relationship that is distal to the radiation window 115. The probe 101 also includes a first proximal electrode 141 located along the probe body 111 in a spatial relationship that is proximal to the radiation window 115 and a second proximal electrode 143 located along the probe body 111 in a spatial relationship that is proximal to the first proximal electrode 141 and proximal to the radiation window 115.

The system further includes a radiofrequency energy source 153 connected to the first distal electrode 131 with a first distal lead 136 and connected to the first proximal electrode 141 with a first proximal lead 146. A sensing circuit 153 is connected to the first distal electrode 131 and first proximal electrode 141. The sensing circuit 153 is configured to generate at least one signal corresponding to an impedance of tissue 181. The system can further include a second distal lead 148 connected to the second proximal electrode 143, and the second distal lead 148 is also connected to the sensing circuit 153.

Figure 2:
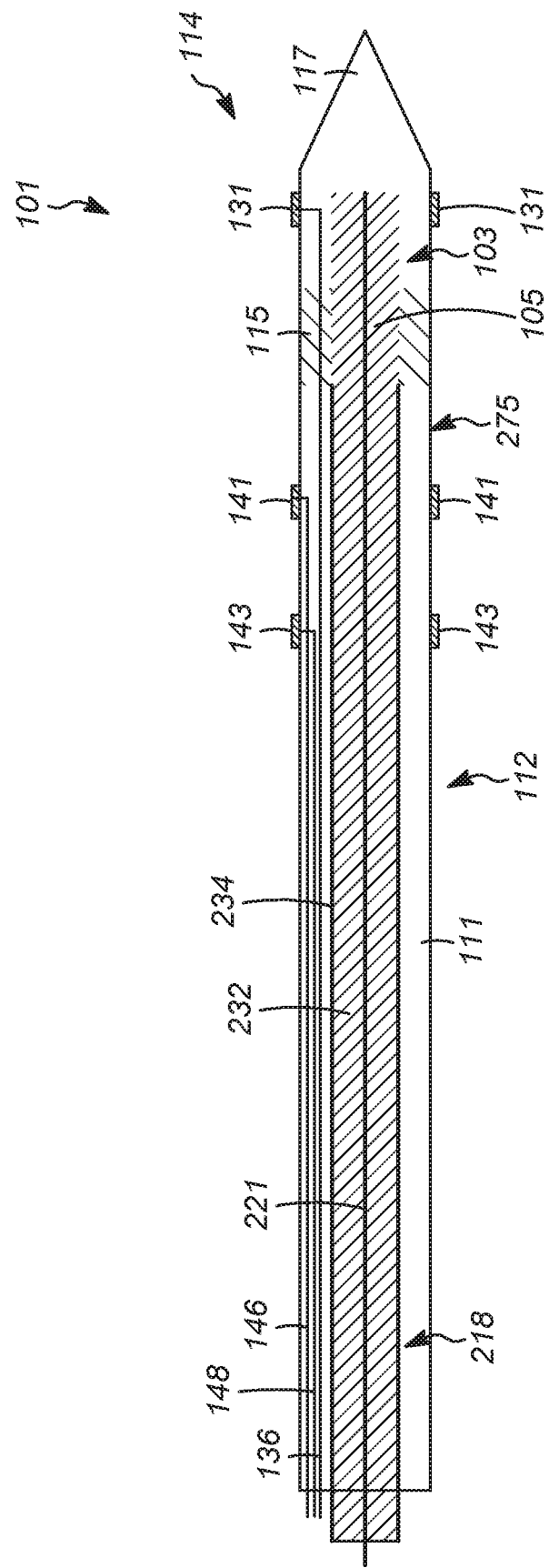
FIG. 2 is a schematic cross-sectional view of the microwave ablation probe of FIG. 1.

With reference to FIG. 2, the probe 101 further includes a cable 218 within the probe body 111. The cable 218 can be a coaxial cable having an outer diameter of at least about 0.5 millimeters, at least about 0.7 millimeters, at most about 2 millimeters, at most about 5 millimeters, ranging from about 0.5 to about 5 millimeters, or ranging from about 0.7 to about 2 millimeters. The cable 218 can be a coaxial cable having an outer diameter of about 0.864 millimeters, commercially available as part no. UT-034 from Micro-Coax, a Carlisle Interconnect Technologies Company, of Scottsdale, Ariz. The cable 218 has at least one conductor, which can be an inner conductor 221. The cable 218 includes a dielectric 232 and an outer conductor 234.

The cable 218 is connected to the antenna 103. The cable 218 connects the antenna 103 to a microwave energy source 151. In some examples, the sensing circuit 153 is configured to sense a first impedance between the first distal electrode 131 and a reference patch 191 on an external surface 192 of a body and a second impedance between the first proximal electrode 141 and the reference patch 191. In some examples, the sensing circuit 153 is configured to sense a first bipolar impedance between the first distal electrode 131 and the first proximal electrode 141. In some examples, a second proximal electrode 143 is located along the probe body 111 proximal to the radiation window 115.

In some examples, the sensing circuit 153 is configured to sense a first bipolar impedance between the first proximal electrode 141 and the second proximal electrode 143. In further examples, the sensing circuit 153 is configured to sense a second bipolar impedance between the first distal electrode 131 and the first proximal electrode 141 and a third bipolar impedance between the first distal electrode 131 and the second proximal electrode 143.

In some examples, the radiofrequency energy source 153 is connected to the second proximal electrode 143 with a second proximal lead 148. In some examples, the sensing circuit 153 is configured to generate at least one signal corresponding to an impedance of tissue 181 between each combination of the first distal electrode 131, the first proximal electrode 141, and the second proximal electrode 143. In further examples, the sensing circuit 153 is configured to generate at least one signal corresponding to an impedance of tissue 181 between the reference patch 191 and each of the first distal electrode 131, the first proximal electrode 141, and the second proximal electrode 143. Placing sensing electrodes at multiple points along the probe body 111 allows the system to provide information about the condition of patient tissue in multiple portions of the tissue to be ablated 183.

Due to the inverse square law of radiation intensity, which states that the intensity of radiation from a source is inversely proportional to the square of the distance from the radiation source, tissue near the radiation window 115 will experience a higher amount of microwave energy. An impedance change over time between the first distal electrode 131 and the first proximal electrode 141 may be different than the impedance change over time between the first distal electrode 131 and the second proximal electrode 143, which may be different than the impedance change over time between the first proximal electrode 141 and the second proximal electrode 143. Similarly, impedance changes over time measured using monopole radiofrequency sensing between the various electrodes along the probe body 111 and the reference patch 191 may differ. These multiple measurements of impedance changes provide the system with a more granular picture of the changes in the patient tissue and tissue necrosis during the ablation procedure.

FIG. 2 is a schematic cross-sectional view of the microwave ablation probe of FIG. 1. In some examples, the first distal electrode 131, the first proximal electrode 141, and the second proximal electrode 143 each comprise a band located on an exterior surface 275 of the probe body 111. In some examples, the bands extend around the circumference of the probe body 111. The electrode can be a platinum marker band with a length about 0.5 millimeters to 5 millimeters. In some examples, the length of the band can be about 1 millimeter. During the microwave ablation treatment, each of the electrodes 131, 141, and 143 are present inside of the patient tissue 181. In some examples, during the microwave ablation treatment, each of the electrodes 131, 141, 143 is present inside of the mass of tissue 183 that is desired to be ablated.

FIGS. 3-7 provide alternative examples of microwave ablation probes that can be used with the system of FIG. 1.

Figure 3:
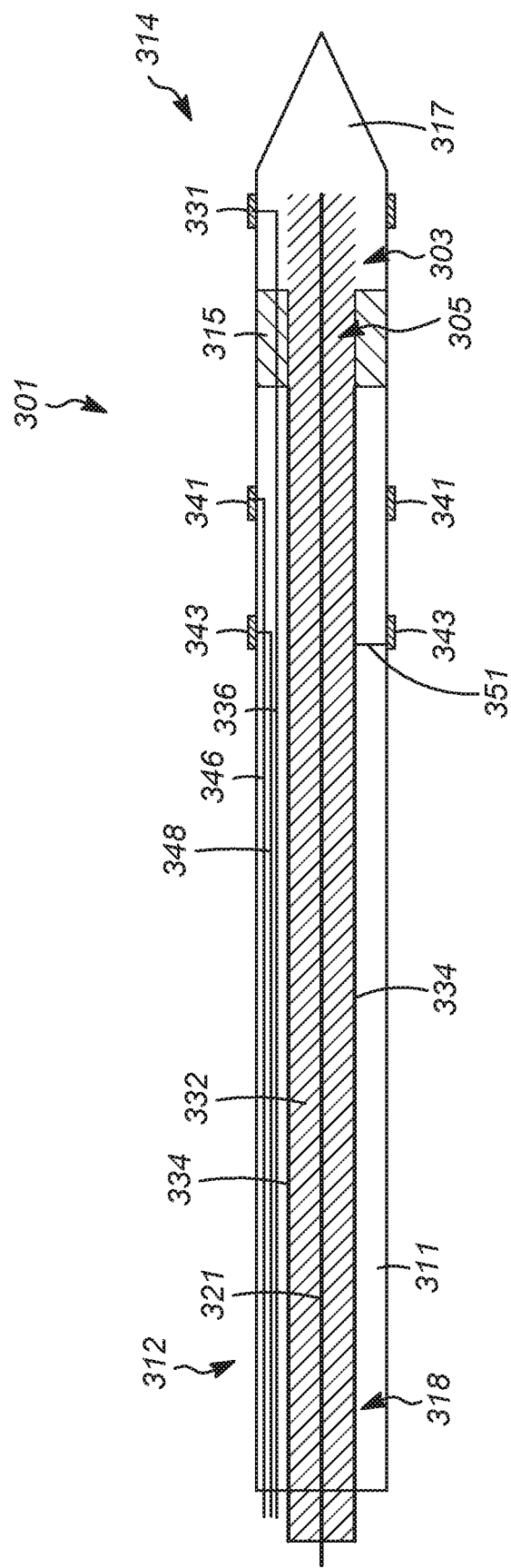
FIG. 3 is a schematic cross-sectional view of a microwave ablation probe according to some examples.

FIG. 3 is a schematic cross-sectional view of a microwave ablation probe 301 according to some examples. The probe 301 comprises a probe body 311, which has a distal tip 317. The probe 301 has a distal end 314 and a proximal end 312. A cable 318, which can be a coaxial cable, comprises an inner conductor 321, and outer conductor 334, and a dielectric 332 insulating the conductors 321, 334.

The probe 301 includes a microwave antenna 303 within the probe body 311. The microwave antenna 303 has a radiating portion 305. The radiating portion 305 is aligned with the window portion 315 of the probe body 311 such that microwave energy emitted from the radiating portion 305 can pass through the window portion 315 into the tissue to be ablated. The radiating portion 305 is generally located near the distal portion 314 of the probe body 311.

The probe 301 further includes a first distal electrode 331 located along the probe body 311 in a spatial relationship that is distal to the radiation window 315. The probe 301 also includes a first proximal electrode 341 located along the probe body 311 in a spatial relationship that is proximal to the radiation window 315, and a second proximal electrode 343 located along the probe body 311 in a spatial relationship that is proximal to the first proximal electrode 341 and proximal to the radiation window 315.

In this alternative example of a microwave ablation probe 301, the second proximal electrode 343 also acts as a choke with a conductive path 351 to outer conductor 334. The second electrode 343 is disposed around the probe body 311. The second electrode 343 acts as a choke because it is electrically connected to the outer conductor 334 by a conductive path 351, which provides a short to the microwave energy source. The choke prevents back propagation of microwave energy, which prevents undesirable heating at the proximal end 312 along the probe body 311. The presence of the choke can also cause the shape of the ablation lesion to be more round in shape compared to if the choke was not present.

In the example of FIG. 3, the first distal electrode 331 is connected to a sensing circuit by a first distal lead 336. The first proximal electrode 341 is connected to a sensing circuit by a first proximal lead 346. The second proximal electrode 343 is connected to a sensing circuit by a second proximal lead 348. Bipolar radiofrequency impedances can be measured at a first time and at a second time later than the first time between any combination of the electrodes 331, 341, and 343.

An electrode that is shorted to the microwave energy source, such as electrode 343, does not simultaneously function as a choke and an impedance sensor. One method is to alternate the function of the electrode to act as a choke while the system is performing ablation, and to act as an impedance sensor before ablation, after ablation, or both before and after ablation. In some examples, the electrode performs the choke function for the majority of the time during the medical procedure. Alternatively, filtering can be used in the sensing and microwave ablation circuitry to avoid interference.

Changes in the impedances corresponding to changes in patient tissue can be calculated for each combination of these electrodes. As in the example of FIG. 2, monopolar radiofrequency impedances can be measured between the electrodes 331, 341, and 343 and a reference patch located on the patient's skin.

Figure 8:
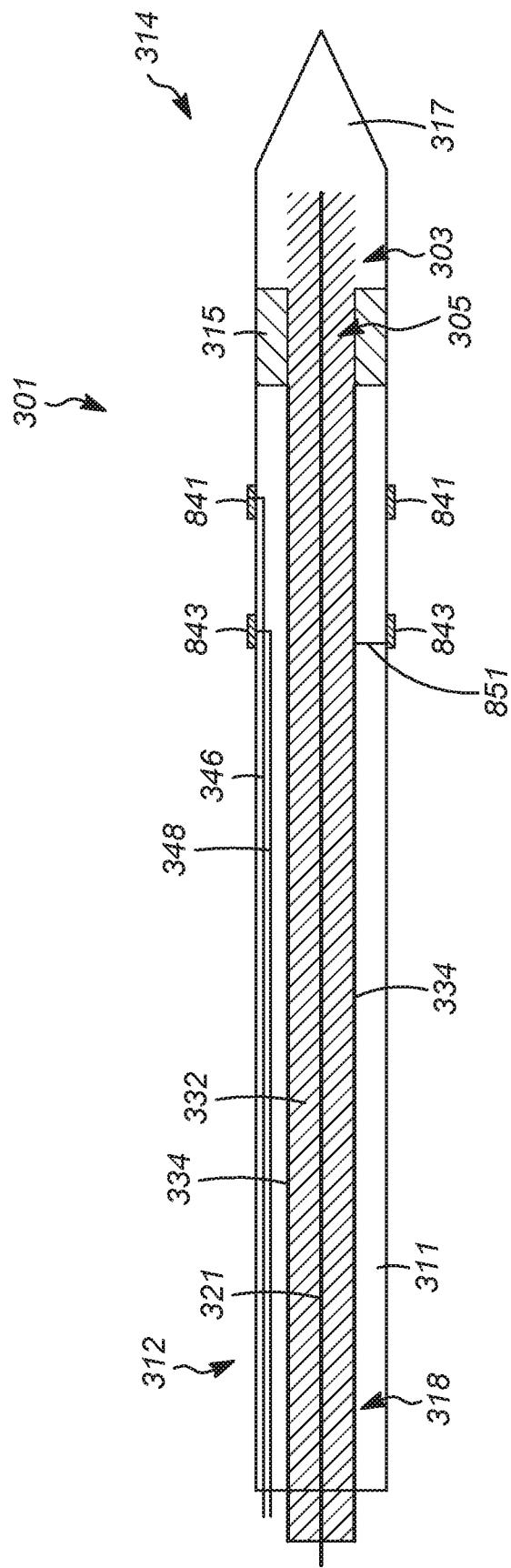
FIG. 8 is a schematic cross-sectional view of a microwave ablation probe according to some examples.

In an alternative example shown in FIG. 8, the system of FIG. 3 can be implemented as a system with a first electrode 841 and a second electrode 843, and no distal electrode. In the example of FIG. 8, the first electrode 841 is a first proximal electrode and the second electrode 843 is a second proximal electrode. It is also possible for more than two proximal electrodes to be provided.

Figure 4:
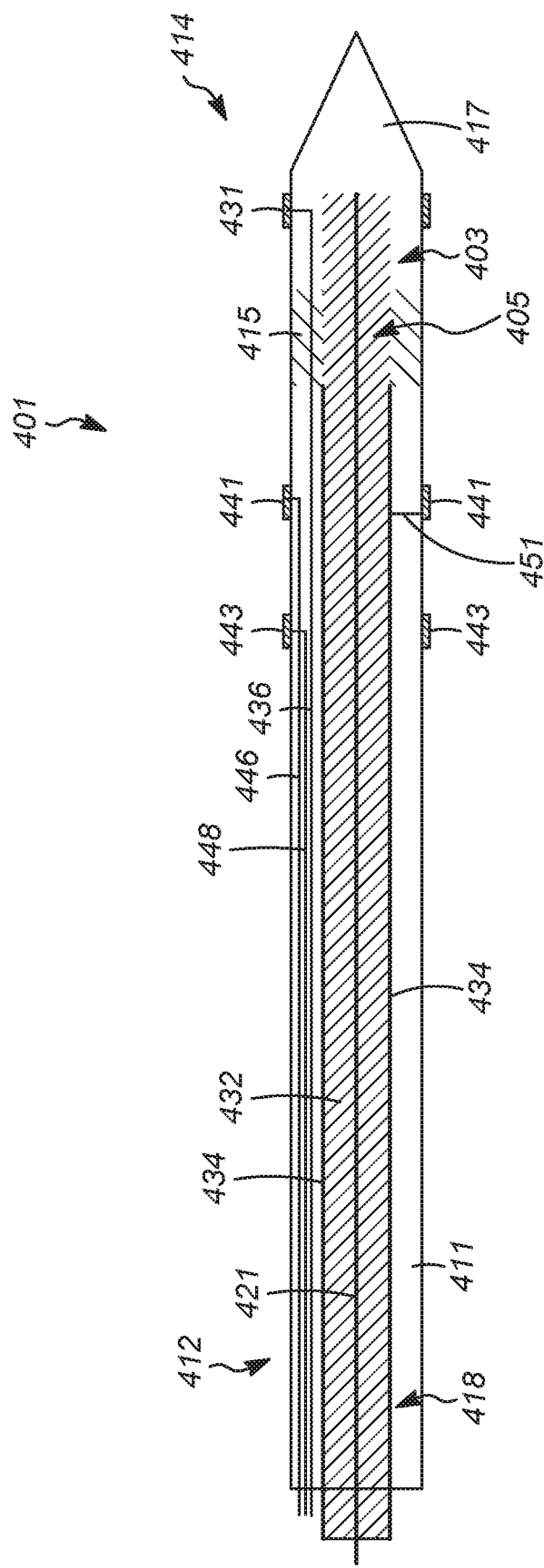
FIG. 4 is a schematic cross-sectional view of a microwave ablation probe according to some examples.

In this example, the distal electrode and corresponding first distal lead are not needed. Bipolar radiofrequency impedance can be measured between the first and second proximal electrodes 841 and 843. Changes in the impedance corresponding to the changes in the tissue can be calculated. Monopolar radiofrequency impedance can also be measured between electrode 841 and a reference patch 191 (see FIG. 1) located on the patient's skin, and between the electrode 843 and the reference patch. The second proximal electrode 843 also acts as a choke with a conductive path 851 to outer conductor 334. As in the example of FIG. 3, the electrode 843 does not simultaneously function as a choke and an impedance sensor. This limitation can be overcome as detailed above with respect to FIG. 3. FIG. 4 is a schematic cross-sectional view of a microwave ablation probe 401 according to some examples. The probe 401 comprises a probe body 411, which has a distal tip 417. The probe 401 has a distal end 414 and a proximal end 412. A cable 418, which can be a coaxial cable, comprises an inner conductor 421, and outer conductor 434, and a dielectric 432 insulating the conductors 421, 434.

The probe 401 includes a microwave antenna 403 within the probe body 411. The microwave antenna 403 has a radiating portion 405. The radiating portion 405 is aligned with the window portion 415 of the probe body 411 such that microwave energy emitted from the radiating portion 405 can pass through the window portion 415 into the tissue to be ablated. The radiating portion 405 is generally located near the distal portion 414 of the probe body 411.

The probe 401 further includes a first distal electrode 431 located along the probe body 411 in a spatial relationship that is distal to the radiation window 415. The probe 401 also includes a first proximal electrode 441 located along the probe body 411 in a spatial relationship that is proximal to the radiation window 415, and a second proximal electrode 443 located along the probe body 411 in a spatial relationship that is proximal to the first proximal electrode 441 and proximal to the radiation window 415.

In this alternative example of a microwave ablation probe 401, the first proximal electrode 441 also acts as a choke with a conductive path 451 to outer conductor 434. The electrode 441 is disposed around the probe body 411. The electrode 441 acts as a choke because it is electrically connected to the outer conductor 434 by a conductive path 451. The choke prevents back propagation of microwave energy, which prevents undesirable heating at the proximal end 412 along the probe body 411. The presence of the choke can also cause the shape of the ablation lesion to be more round shaped than without a choke. As in the example of FIG. 3, the electrode 441 does not simultaneously function as a choke and an impedance sensor. This limitation can be overcome as detailed above with respect to FIG. 3.

In the example of FIG. 4, the first distal electrode 431 is connected to a sensing circuit by a first distal lead 436. The first proximal electrode 441 is connected to a sensing circuit by a first proximal lead 446. The second proximal electrode 443 is connected to a sensing circuit by a second proximal lead 448. Bipolar radiofrequency impedances can be measured at a first time and at a second time later than the first time between any combination of the electrodes 431, 441, and 443. Changes in the impedances corresponding to changes in patient tissue can be calculated for each combination of these electrodes. As in the example of FIG. 2, monopolar radiofrequency impedances can be measured between the electrodes 431, 441, and 443 and a reference patch located on the patient's skin.

Figure 5:
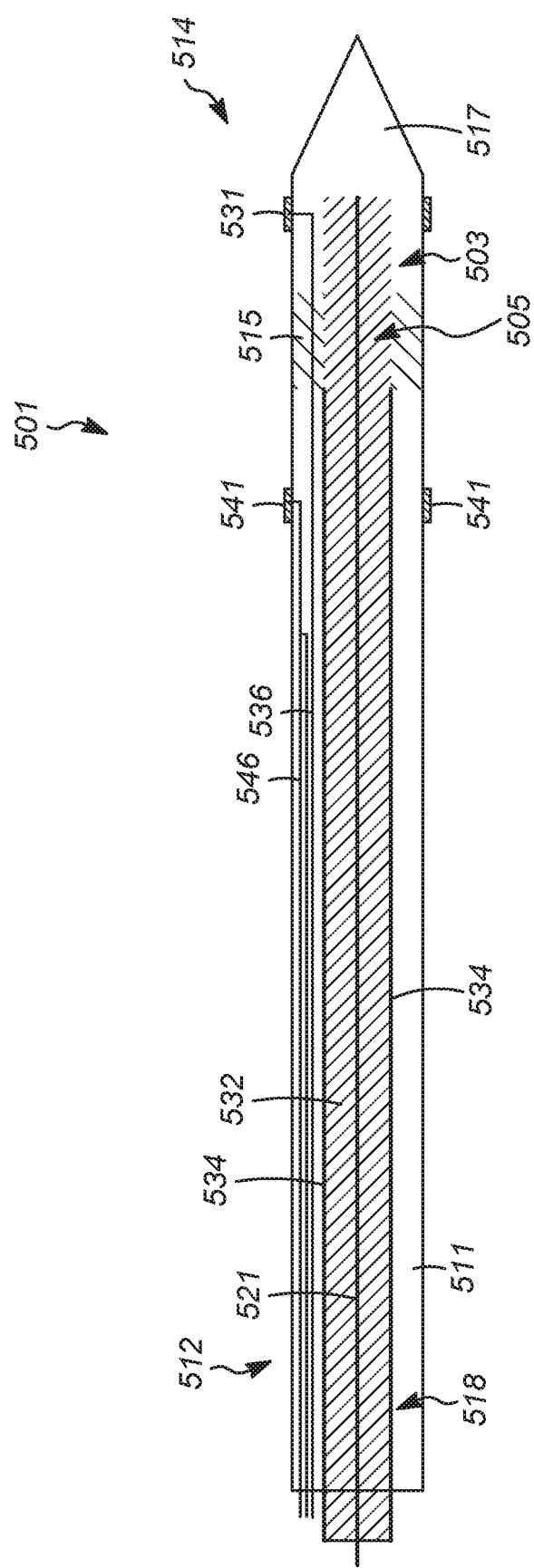
FIG. 5 is a schematic cross-sectional view of a microwave ablation probe according to some examples.

FIG. 5 is a schematic cross-sectional view of a microwave ablation probe 501 according to some examples. The probe 501 comprises a probe body 511, which has a distal tip 517. The probe 501 has a distal end 514 and a proximal end 512. A cable 518, which can be a coaxial cable, comprises an inner conductor 521, and outer conductor 534, and a dielectric 532 insulating the conductors 521, 534.

The probe 501 includes a microwave antenna 503 within the probe body 511. The microwave antenna 503 has a radiating portion 505. The radiating portion 505 is aligned with the window portion 515 of the probe body 511 such that microwave energy emitted from the radiating portion 505 can pass through the window portion 515 into the tissue to be ablated. The radiating portion 505 is generally located near the distal portion 514 of the probe body 511.

The probe 501 further includes a first distal electrode 531 located along the probe body 511 in a spatial relationship that is distal to the radiation window 515. The probe 501 also includes a first proximal electrode 541 located along the probe body 511 in a spatial relationship that is proximal to the radiation window 515. In some examples (not shown), the proximal electrode 541 could be a choke.

In the example of FIG. 5, the first distal electrode 531 is connected to a sensing circuit by a first distal lead 536. The first proximal electrode 541 is connected to a sensing circuit by a first proximal lead 546. Bipolar radiofrequency impedances can be measured at a first time and at a second time later than the first time between any combination of the electrodes 531, 541. Changes in the impedances corresponding to changes in patient tissue can be calculated for each combination of these electrodes. As in the example of FIG. 2, monopolar radiofrequency impedances can be measured between the electrodes 531, 541 and a reference patch located on the patient's skin.

Figure 6:
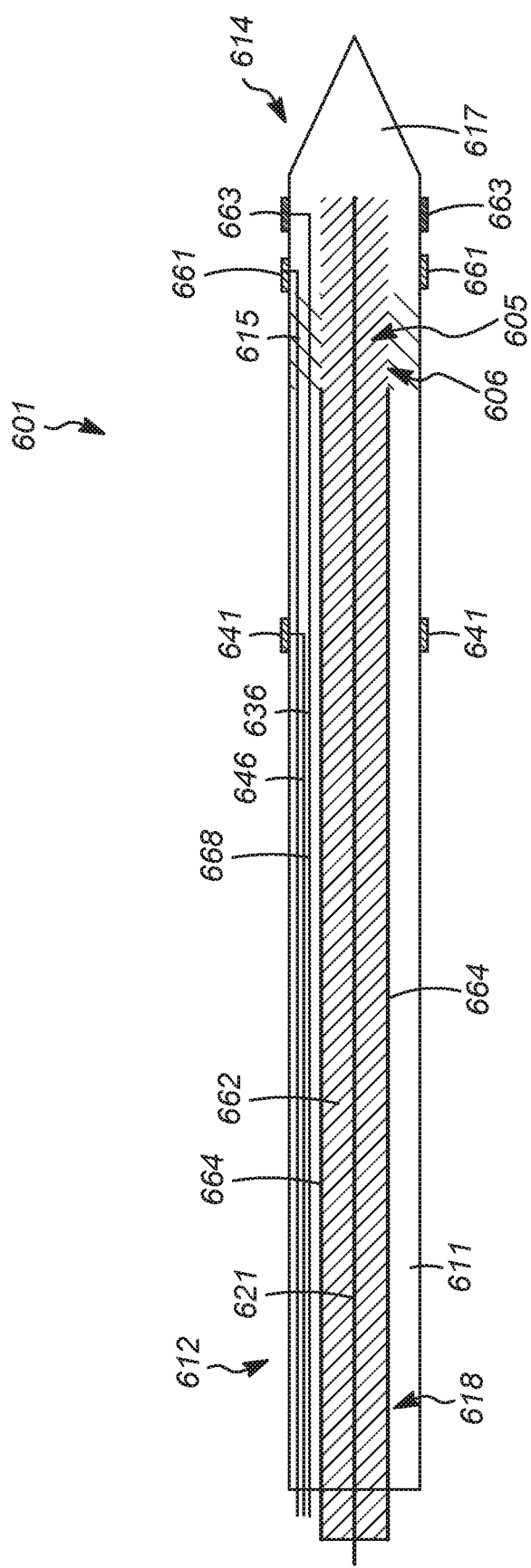
FIG. 6 is a schematic cross-sectional view of a microwave ablation probe according to some examples.

FIG. 6 is a schematic cross-sectional view of a microwave ablation probe 601 according to some examples. The probe 601 comprises a probe body 611, which has a distal tip 617. The probe 601 has a distal end 614 and a proximal end 612. A cable 618, which can be a coaxial cable, comprises an inner conductor 621, and outer conductor 664, and a dielectric 662 insulating the conductors 621, 664.

The probe 601 includes a microwave antenna 606 within the probe body 611. The microwave antenna 606 has a radiating portion 605. The radiating portion 605 is aligned with the window portion 615 of the probe body 611 such that microwave energy emitted from the radiating portion 605 can pass through the window portion 615 into the tissue to be ablated. The radiating portion 605 is generally located near the distal portion 614 of the probe body 611.

The probe 601 further includes a first distal electrode 661 located along the probe body 611 in a spatial relationship that is distal to the radiation window 615, and a second distal electrode 663 located along the probe body 611 in a spatial relationship that is distal to the first distal electrode 661 and distal to the radiation window 615. The probe 601 also includes a first proximal electrode 641 located along the probe body 611 in a spatial relationship that is proximal to the radiation window 615. In some examples (not shown), the proximal electrode 641 could be a choke.

In the example of FIG. 6, the first distal electrode 661 is connected to a sensing circuit by a first distal lead 636. The first proximal electrode 641 is connected to a sensing circuit by a first proximal lead 646. The second distal electrode 663 is connected to a sensing circuit by a second distal lead 668. Bipolar radiofrequency impedances can be measured at a first time and at a second time later than the first time between any combination of the electrodes 661, 641, and 663. In some examples, the sensing circuit is configured to sense a first bipolar impedance between the first distal electrode 661 and the second distal electrode 663. Changes in the impedances corresponding to changes in patient tissue can be calculated for each combination of these electrodes. As in the example of FIG. 2, monopolar radiofrequency impedances can be measured between the electrodes 661, 663, and 641 and a reference patch located on the patient's skin.

Figure 7:
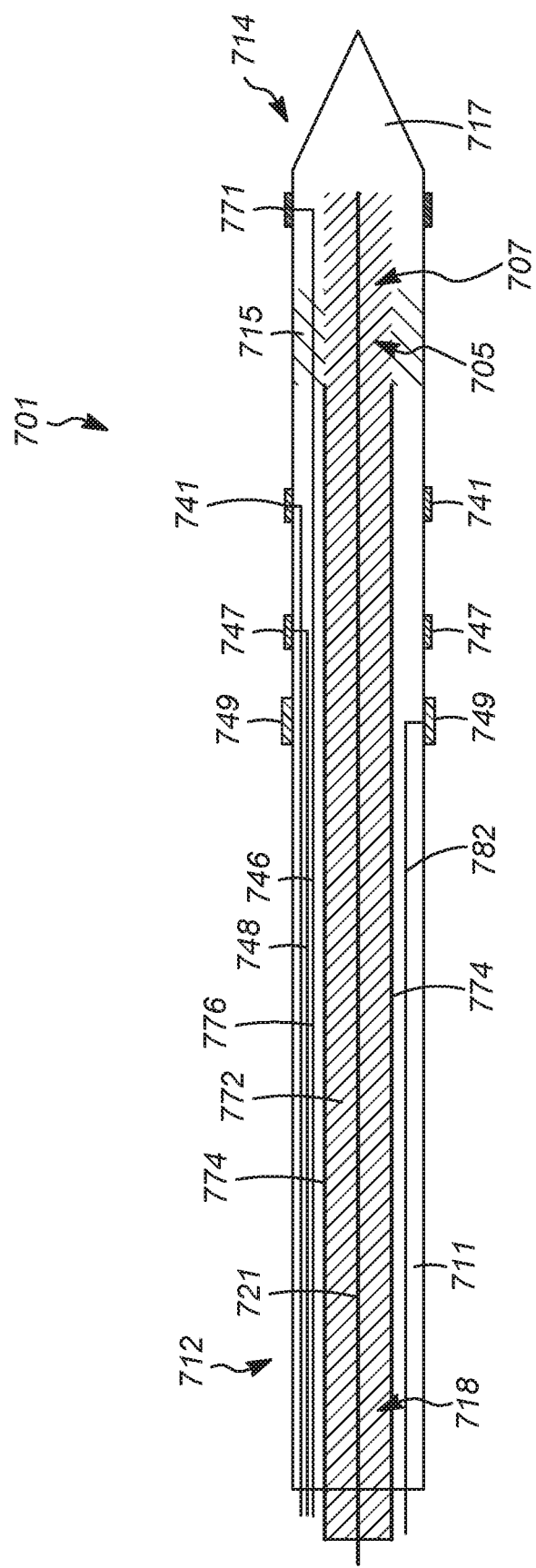
FIG. 7 is a schematic cross-sectional view of a microwave ablation probe according to some examples.

FIG. 7 is a schematic cross-sectional view of a microwave ablation probe 701 according to some examples. The probe 701 comprises a probe body 711, which has a distal tip 717. The probe 701 has a distal end 714 and a proximal end 712. A cable 718, which can be a coaxial cable, comprises an inner conductor 721, and outer conductor 774, and a dielectric 772 insulating the conductors 721, 774.

The probe 701 includes a microwave antenna 707 within the probe body 711. The microwave antenna 707 has a radiating portion 705. The radiating portion 705 is aligned with the window portion 715 of the probe body 711 such that microwave energy emitted from the radiating portion 705 can pass through the window portion 715 into the tissue to be ablated. The radiating portion 705 is generally located near the distal portion 714 of the probe body 711.

The probe 701 further includes a first distal electrode 771 located along the probe body 711 in a spatial relationship that is distal to the radiation window 715. The probe 701 also includes a first proximal electrode 741 located along the probe body 711 in a spatial relationship that is proximal to the radiation window 715, and a second proximal electrode 747 located along the probe body 711 in a spatial relationship that is proximal to the first proximal electrode 741 and proximal to the radiation window 715. In some examples, the probe 701 further includes a third proximal electrode 749 located along the probe body 711 proximal to the second proximal electrode 747 and the radiation window 715. In some examples (not shown), one of the proximal electrodes 741, 747, 749 could be a choke.

In the example of FIG. 7, the first distal electrode 771 is connected to a sensing circuit by a first distal lead 776. The first proximal electrode 741 is connected to a sensing circuit by a first proximal lead 746. The second proximal electrode 747 is connected to a sensing circuit by a second proximal lead 748. The third proximal electrode 749 is connected to a sensing circuit by a third proximal lead 782. Bipolar radiofrequency impedances can be measured at a first time and at a second time later than the first time between any combination of the electrodes 771, 741, 747, and 749. In these examples, the sensing circuit is configured to sense an impedance between each combination of the first distal electrode 771, the first proximal electrode 741, the second proximal electrode 747, and the third proximal electrode 749. Changes in the impedances corresponding to changes in patient tissue can be calculated for each combination of these electrodes. As in the example of FIG. 2, monopolar radiofrequency impedances can be measured between the electrodes 771, 741, 747, 749 and a reference patch located on the patient's skin.

Figure 9:
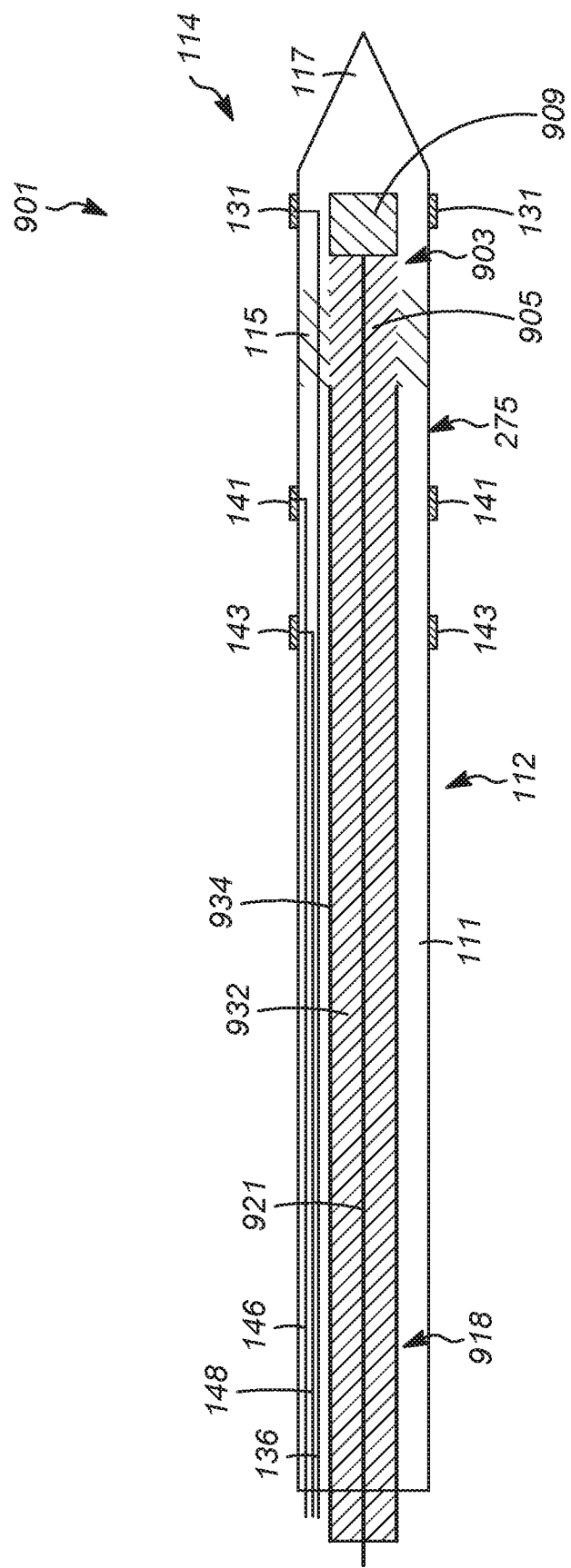
FIG. 9 is a schematic cross-sectional view of a microwave ablation probe according to some examples.

FIG. 9 is a schematic cross-sectional view of a microwave ablation probe 901 according to some examples. The probe 901 is similar to the probe 101 described in relation to FIG. 2, and contains similar features. The probe 901 utilizes a dipole microwave antenna 903 having a radiating portion

905. The dipole microwave antenna 903 comprises a cable 918 that can be a coaxial cable having an inner conductor 921, an outer conductor 934, and a dielectric 932 insulating the conductors 921, 934. The dipole microwave antenna 903 further comprises a conductive end member 909 that forms part of the antenna 903. The probe 901 has first and second proximal electrodes 141, 143 and a distal electrode 131.

Microwave Ablation Methods

During ablation treatment, a physician can adjust a number of parameters in the microwave ablation system to create the desired ablation lesion. The parameters can alternatively be automatically adjusted by a controller in a computer system. The amount of power provided to a microwave energy source can be adjusted. A higher or lower amount of power to be delivered either increases or decreases the intensity of the microwave radiation entering the tissue. Ablation at high power can effectively create a large lesion. If the power is too high, negative effects can occur, such as tissue charring. The system can also adjust the amount of time that the microwave radiation is delivered to the tissue. A shorter time period is associated with less risk for charred tissue, however, if the ablation treatment is terminated too early, the treatment may not successfully ablate all of the tissue that is desired to be ablated.

The impedance of the tissue changes while tissue is heated during thermal ablation. When the temperature of the tissue reaches a certain point, typically above about 90 Celsius, the impedance of the tissue begins to increase due to loss of moisture in the tissue.

In some use scenarios, the system can modulate the microwave power delivery to the system in response to a change of impedance at multiple electrode locations. This allows the system to achieve optimal tissue ablation at these locations to avoid both overheating (charring) and underheating (insufficient tissue ablation). When the impedance change indicates that tissue is overheated, the microwave ablation system can reduce power or terminate the delivery of microwave energy. When the impedance change indicates that tissue is underheated, such as when heat is transferred away due to the presence of a blood vessel, the microwave ablation system can increase power to compensate for this additional convection.

The microwave ablation system of the current disclosure can be used to perform a method. The microwave ablation system includes a microwave ablation probe and an antenna with a radiating portion for emitting microwave energy. The probe has a probe body with a radiation window portion that is at least partially transparent to microwave energy. The radiating portion is aligned with the window portion of the probe body. The probe includes a first distal electrode located along the probe body distal to the window portion and a first proximal electrode located along the probe body proximal to the radiation window portion.

In the method, the probe body of the microwave ablation probe is inserted into patient tissue, and positioned at a location of tissue to be ablated. Microwave energy is generated by a generator, and then the microwave energy is transmitted to the radiating portion of the probe. The microwave energy is emitted from inside of the probe body to the outside of the probe via the transparent window portion of the probe. As the microwave energy penetrates the tissue, the tissue becomes heated, and a lesion is formed.

In the described microwave ablation method, the impedance of the tissue is measured at a first time. For example, the impedance can be measured before ablation is started or close to the beginning of the procedure. Later, the impedance of the tissue is measured a second time. The second measurement can be taken, for example, after a predetermined amount of time. The impedance measurement can also be taken periodically throughout the procedure. Alternatively, the impedance measurement can be monitored continuously. The first impedance is compared to the second impedance to determine whether a change in impedance has occurred. If the impedance has changed, such as when the tissue begins to form a lesion or the tissue becomes charred, steps can be taken to change therapeutic parameters.

The impedance measurement can be taken a number of different ways with the various examples described herein. In one example, radiofrequency energy is delivered to an electrode and the impedance is measured between the electrode and a reference patch on the patient's skin. In this case, the system is a monopolar system. A bipolar system can also be used. For example, radiofrequency energy can be delivered to a first electrode and to a second electrode, and the impedance between the first and second electrodes can be measured. The impedance can be measured using a sensing circuit such as that described above with reference to FIG. 1.

The multiple sensing electrodes can be used to develop a clearer picture of the actual change in tissue inside of the patient's body. In a system with one distal electrode and two proximal electrodes in combination with a reference patch, impedance can be measured using monopolar sensing between the first distal electrode and the reference patch, between the first proximal electrode and the reference patch, and between the second proximal electrode and the reference patch. Additionally, impedance can be measured using bipolar sensing between the first distal electrode and the first proximal electrode; between the first distal electrode and the second proximal electrode; and between the first proximal electrode and the second proximal electrode. One or more of these impedance measurements are taken. The measurement is then saved in memory, such as in a computer memory.

At a later time, the impedance measurement or measurements are taken again. Depending upon the particular patient and the particular treatment being applied, the different impedance measurements can change at different rates. The difference in change in impedance can provide the system with information about the progress of the treatment. If it is found that impedance has increased above a certain threshold, the ablation treatment can be terminated.

Electrode Leads

The radiation window can be defined by a microwave shielding structure. As detailed above with respect to FIGS. 2-7, the microwave ablation probe includes one or more distal leads connected to one or more distal sensing electrodes and one or more proximal leads connected to one or more proximal sensing electrodes. Each of these leads is electrically isolated from the microwave ablation antenna. In some examples, the leads are configured to be underneath the microwave shielding structure. In alternative examples, the leads can be outside of the microwave shielding structure and underneath an insulation layer. In addition or alternatively, the leads can comprise a conductive trace on an outside surface of the microwave shielding structure. In one example, the leads comprise a conductive trace on an outside surface of the microwave shielding underneath an insulation layer. The insulating layer can include a material made of polyether ether ketone (PEEK), polytetrafluoroethylene (PTFE), fluorinated ethylene propylene (FEP), polyimide (PI), or combinations of these materials.

Microwave Ablation Antennas

In the examples provided in FIGS. 1-7, the microwave ablation antenna is a coaxial monopolar antenna. However, alternative antenna designs are contemplated. The system can alternatively use a slot antenna, a dipole antenna, a triaxial antenna, or a choked slot antenna. Such systems are detailed in Brace, *Microwave Tissue Ablation: Biophysics, Technology, and Applications*, Critical Reviews™ in Biomedical Engineering, 38(1):65-78 (2010), the entirety of which is herein incorporated by reference. In some embodiments, the electrodes used as impedance sensors are not placed within the antenna radiation section to avoid interference.

Ablation and Sensing Control System

With reference to FIG. 1, a microwave ablation and radiofrequency sensing control system 169 is provided. The control system 169 comprises a user input 163 and a display 165, allowing a physician or other medical professional to monitor and interact with the control system 169. A controller 161 is configured to operate the various functions of the control system 169. The control system 169 has a microwave energy source 151 for providing microwave energy to the microwave ablation probe 101 during an ablation treatment. The control system 169 further includes a radiofrequency energy source 153 separate from the microwave energy source 151. The radiofrequency energy source 153 is configured to provide radiofrequency energy to the sensing electrodes in the probe 101. The radiofrequency energy source 153 can be used with bipolar sensing, monopolar sensing, or both. An available microwave ablation generator is the Sairem GMS solid state generator, operating at 200 W and 2450 MHz, manufactured by Sairem, of Neyron, France. Alternatively, the Emblation Microwave MSYS245 Medical System, operating at 100 W and 2450 MHz, manufactured by Emblation Microwave, an Emblation Limited Company, of Scotland, UK can be used. These commercial systems and any combination can be used to implement the system described herein. These functions can also be realized by a dedicated system with both microwave generator and radiofrequency impedance measurement capabilities.

In addition, or alternatively, the control system is configured to use the impedance of the tissue from an impedance sensing circuit to detect a change in the tissue due to microwave ablation.

Radiofrequency Impedance Sensing Circuit

For purposes of illustration, the various figures show at least two electrodes. Each electrode is wired and connected to a radiofrequency impedance sensing circuit. The sensing circuit is configured to generate at least one signal corresponding to an impedance of tissue.

In some examples, radiofrequency energy working at a frequency between about 5 kHz and 10 MHz is used. In some examples, the radiofrequency impedance sensing circuit can be operated in frequency of about 20 kHz.

In some implementations, the sensing circuit produces a small electrical current, between the range of 10 μA to 10 mA, and measures the voltage between the bipolar sensing electrodes or between the monopolar sensing electrodes and a reference patch located on the patient's skin. Alternatively, the sensing circuit can apply a small voltage, between 1 millivolt and 1 Volt, and measure the electrical current between the electrodes. The voltage and current are used to calculate both resistance and reactance, or impedance amplitude and phase angle.

An available radiofrequency measurement system is the Keysight E4980A Precision LCR Meter, produced by Keysight of Santa Rosa, Calif. Another available radiofrequency measurement system is the Hioki LCR Meter IM3536, from Hioki USA Corporation of Cranbury, N.J. Alternatively, radiofrequency measurement devices can be incorporated into a dedicated system for controlling the microwave ablation probe.

Cooling System for Microwave Ablation Probe

The microwave ablation system 100 can further include a cooling system (not shown). The cooling system can be, for example, a closed loop system in which a cooling fluid is transmitted along the probe body from outside of the probe toward the distal end of the probe, then back toward the proximal end of the probe and out of the probe. Alternatively, the cooling system can be an open irrigation system in which a cooling fluid, such as a saline solution, is transmitted from outside of the probe, through the probe body, and out of the probe at a distal end 114 of the probe. An open irrigation system can provide irrigation proximal to the radiating portion of the microwave antenna, distal to the radiating portion of the microwave antenna, or both.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this disclosed technology pertains. All publications and patent applications are herein incorporated by reference to the same extent as if each individual publication or patent application was specifically and individually indicated by reference.

The embodiments described herein are not intended to be exhaustive or to limit the disclosed technology to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A microwave ablation system having:
   an elongate microwave ablation probe comprising:
      a probe body comprising a radiation window that is at least partially transparent to microwave energy;
      an antenna within the probe body, the antenna having a radiating portion for emission of microwave energy at a distal portion of the probe body, wherein the radiating portion is aligned with the radiation window;
      a cable within the probe body, connected to the antenna, comprising at least one conductor;
      a first distal electrode located along the probe body distal to the radiation window; and
      a first proximal electrode located along the probe body proximal to the radiation window, wherein the first proximal electrode is a choke of the microwave ablation probe disposed around the probe body at least when the antenna is emitting the microwave energy;
a microwave energy source connected to the antenna via the cable;
a radiofrequency energy source connected to the first distal electrode with a first distal lead and connected to the first proximal electrode with a first proximal lead; and
a sensing circuit connected to the first distal electrode and first proximal electrode, the sensing circuit configured to generate at least one signal corresponding to an impedance of tissue.

2. The system of claim 1 wherein the sensing circuit is configured to sense a first impedance between the first distal electrode and a reference patch on an external surface of a body and a second impedance between the first proximal electrode and the reference patch.

3. The system of claim 1 wherein the sensing circuit is configured to sense a first bipolar impedance between the first distal electrode and the first proximal electrode.

4. The system of claim 1 further comprising a second distal electrode located along the probe body distal to the radiation window.

5. The system of claim 4 wherein the sensing circuit is configured to sense a first bipolar impedance between the first distal electrode and the second distal electrode.

6. The system of claim 1 further comprising a second proximal electrode located along the probe body proximal to the radiation window.

7. The system of claim 6 wherein the sensing circuit is configured to sense a first bipolar impedance between the first proximal electrode and the second proximal electrode.

8. The system of claim 7 wherein the sensing circuit is configured to sense a second bipolar impedance between the first distal electrode and the first proximal electrode and a third bipolar impedance between the first distal electrode and the second proximal electrode.

9. The system of claim 1 wherein the first distal electrode or first proximal electrode comprises a band located on an exterior surface of the probe body.

10. The system of claim 1 wherein the probe body further comprises a microwave shielding structure defining the radiation window, wherein the first distal lead and first proximal lead are electrically isolated from the antenna and are configured to be from a group consisting of:
underneath the microwave shielding structure,
outside of the microwave shielding structure and underneath an insulation layer, and
a conductive trace on an outside surface of the microwave shielding structure.

11. The system of claim 1 wherein the first proximal electrode is an impedance sensor of the microwave ablation probe when the antenna is not emitting the microwave energy.

12. A microwave ablation system having:
an elongate microwave ablation probe comprising:
a probe body comprising a radiation window that is at least partially transparent to microwave energy;
an antenna within the probe body, the antenna having a radiating portion for emission of microwave energy at a distal portion of the probe body, wherein the radiating portion is aligned with the radiation window;
a cable within the probe body, connected to the antenna, comprising at least one conductor;
a first electrode located along the probe body, wherein the first electrode is a choke of the microwave ablation probe disposed around the probe body at least when the antenna is emitting the microwave energy; and
a second electrode located along the probe body;
a microwave energy source connected to the antenna via the cable;
a radiofrequency energy source connected to the first electrode with a first lead and connected to the second electrode with a second lead; and
a sensing circuit connected to the first electrode and second electrode, the sensing circuit configured to generate at least one signal corresponding to an impedance of tissue, the system configured to use the impedance of tissue to detect a change in tissue due to microwave ablation; and
wherein the sensing circuit is configured to sense a first impedance between the first electrode and a reference patch on an external surface of a body and a second impedance between the second electrode and the reference patch.

13. The system of claim 12 wherein the first electrode is a first proximal electrode located along the probe body proximal to the radiation window and the second electrode is a second proximal electrode located along the probe body proximal to the radiation window.

14. The system of claim 12 wherein the first electrode is a first distal electrode located along the probe body distal to the radiation window and the second electrode is a first proximal electrode located along the probe body proximal to the radiation window.

15. A method of microwave ablation comprising:
providing a microwave ablation system comprising
a probe having a probe body,
an antenna having a radiating portion for emission of microwave energy, wherein the radiating portion is aligned with a window portion that is at least partially transparent to microwave energy,
a first distal electrode located along the probe body distal to the window portion, and a first proximal electrode located along the probe body proximal to the window portion, wherein the first proximal electrode is a choke of the microwave ablation probe disposed around the probe body at least when the antenna is emitting the microwave energy;
delivering microwave energy to the radiating portion;
delivering radiofrequency energy to the first distal electrode and the first proximal electrode;
measuring an impedance of tissue using a sensing circuit connected to the first distal electrode and to the first proximal electrode; and
determining a tissue change using the impedance of tissue measured by the sensing circuit.

16. The method of claim 15 further comprising sampling a first impedance at a first time, sampling a second impedance at a second time, and comparing the first impedance to the second impedance.

17. The method of claim 16 further comprising determining a microwave ablation treatment endpoint based on the comparison of the first impedance to the second impedance.

18. The method of claim 16 further comprising adjusting a therapy parameter based on the comparison of the first impedance to the second impedance, wherein the therapy parameter is selected from a group consisting of: power provided to a microwave energy source and a time length of ablation procedure.

19. The method of claim 15 further comprising:
  measuring a first impedance between the first distal electrode and a reference patch on an external surface of a body, and
  measuring a second impedance between the first proximal electrode and the reference patch.

20. The method of claim 15 further comprising measuring an impedance between the first distal electrode and the first proximal electrode.

\* \* \* \* \*